US012467688B2

(12) United States Patent
Kessell

(10) Patent No.: US 12,467,688 B2
(45) Date of Patent: Nov. 11, 2025

(54) DRYING RACK DEVICE

(71) Applicant: Rita Kessell, Omak, WA (US)

(72) Inventor: Rita Kessell, Omak, WA (US)

( * ) Notice: Subject to any disclaimer, the term of this patent is extended or adjusted under 35 U.S.C. 154(b) by 818 days.

(21) Appl. No.: 17/837,570

(22) Filed: Jun. 10, 2022

(65) Prior Publication Data

US 2023/0074575 A1 Mar. 9, 2023

Related U.S. Application Data

(60) Provisional application No. 63/335,520, filed on Apr. 27, 2022, provisional application No. 63/241,660, filed on Sep. 8, 2021.

(51) Int. Cl.

| | |
|---|---|
| ***F26B 25/18*** | (2006.01) |
| ***A61B 50/22*** | (2016.01) |
| ***A61C 19/00*** | (2006.01) |
| ***F26B 9/00*** | (2006.01) |

(52) U.S. Cl.

CPC ............ *F26B 25/185* (2013.01); *A61B 50/22* (2016.02); *A61C 19/00* (2013.01); *F26B 9/003* (2013.01)

(58) Field of Classification Search

CPC ........ F26B 25/185; F26B 9/003; A61B 50/22; A61B 19/00

USPC ............................................................ 34/511

See application file for complete search history.

(56) References Cited

U.S. PATENT DOCUMENTS

| | | | | |
|---|---|---|---|---|
| 5,659,975 | A * | 8/1997 | Bahner | F26B 23/002 34/619 |
| 6,179,134 | B1 * | 1/2001 | Pine | A47L 19/04 312/228.1 |
| 6,931,756 | B2 * | 8/2005 | Morgan | F26B 21/001 165/61 |
| 9,052,143 | B2 * | 6/2015 | Janowski | F26B 21/12 |
| 9,709,327 | B2 * | 7/2017 | Marchiori | F26B 25/16 |
| 10,674,890 | B1 * | 6/2020 | Armstrong | A47L 19/04 |
| 11,039,731 | B2 * | 6/2021 | Han | A47L 19/04 |
| D964,670 | S * | 9/2022 | Callahan | D32/2 |
| 11,867,461 | B2 * | 1/2024 | Kozlowski | F26B 5/06 |
| 11,925,714 | B2 * | 3/2024 | Moughton | A61L 2/24 |
| 11,944,254 | B2 * | 4/2024 | Thiyagarajan | A47L 15/483 |
| 2023/0074575 | A1 * | 3/2023 | Kessell | A61B 50/22 |
| 2023/0414799 | A1 * | 12/2023 | Hewins | F26B 21/02 |

FOREIGN PATENT DOCUMENTS

| | | | | |
|---|---|---|---|---|
| GB | 2600971 A * | 5/2022 | F26B 21/004 |
| JP | 2021505280 A * | 2/2021 | F26B 3/04 |
| WO | WO-2022101638 A1 * | 5/2022 | A61L 2/26 |

* cited by examiner

*Primary Examiner* — Stephen M Gravini
(74) *Attorney, Agent, or Firm* — Brennan, Manna & Diamond, LLC

(57) ABSTRACT

The present invention relates to a novel drying rack device. The device is designed to save time and effort when cleaning and sterilizing instruments, cassettes, tools, and/or accessories. The device comprises a countertop drying rack that sits on a tray. The countertop drying rack comprises a plurality of compartments that can be round and/or flat, with a plurality of drain holes for air drying wet instruments. Further, the tray below the rack collects water runoff for safe disposal and to allow the instruments to air dry. The device keeps instruments and tools organized, different kits separated, allows instruments to dry, and decreases risk of injury and exposure to bloodborne pathogens.

17 Claims, 7 Drawing Sheets

DRYING RACK DEVICE

CROSS-REFERENCE TO RELATED APPLICATION

The present application claims priority to, and the benefit of, U.S. Provisional Application No. 63/241,660, which was filed on Sep. 8, 2021, and U.S. Provisional Application No. 63/335,520, which was filed on Apr. 27, 2022, both of which are incorporated herein by reference in their entirety.

FIELD OF THE INVENTION

The present invention relates generally to the field of drying rack devices. More specifically, the present invention relates to an improved drying rack device for dental instruments and other loose instruments or instruments contained in a cassette that provides users with a compartmentalized rack that keeps several dental instrument sets organized while they dry. Accordingly, the present disclosure makes specific reference thereto. Nonetheless, it is to be appreciated that aspects of the present invention are also equally applicable to other like applications, devices and methods of manufacture.

BACKGROUND

By way of background, this invention relates to improvements in drying racks of the type which are used to dry dental, medical, orthodontic, and/or veterinary tools, instruments, and/or accessories. The majority of instruments leave the ultrasonic cleaner as loose pieces. If the instruments leave as loose pieces, these loose instruments become mixed up when they are dumped from the ultrasonic cleaner into a pile to dry. This slows the entire sterilization process because instruments must be completely dry and sorted into sets before being packaged for sterilization. Furthermore, sorting sharp instruments increases the risk of users being poked, cut, and exposed to bloodborne pathogens. Additionally, instrument tips can be easily damaged during the sorting process.

Furthermore, some instruments leave the ultrasonic cleaner in metal and/or plastic cassettes sterilization boxes. If the instruments are packaged in cassettes and/or sterilization boxes, the cassettes and/or sterilization boxes end up piled on top of each other or leaning against cabinet walls. This also slows the entire sterilization process because instruments must be completely dry before being sterilized. Thus, in all cases, loose instruments and associated containers create risk, inefficiency, and stress for users when cleaning and/or sterilizing instruments.

Thus, it is necessary for users to have a drying rack device that saves time by speeding up and streamlining the sterilization process, reducing the risk of employee injury and pathogen exposure, and decreasing the number of damaged instruments. Generally, when not using the disclosed drying rack device, users sterilizing instruments have a greater risk of injury and exposure to bloodborne pathogens by being poked or cut by sharp and contaminated instruments when they are untangling and sorting them for sterilization. Therefore, users require a drying rack device that swiftly and easily dries dental, medical, orthodontic, and/or veterinary tools, instruments, and/or accessories.

Therefore, there exists a long-felt need in the art for a drying rack device that provides users with a compartmentalized rack that keeps several instrument sets organized while they dry, eliminating the need to sort them and increasing efficiency. There is also a long-felt need in the art for a drying rack device that eliminates the problem of instrument sets repeatedly being dumped on top of one another and rewetting the entire pile. Further, there is a long-felt need in the art for a drying rack device that features compartments with drain holes and that sits on an accompanying tray. Moreover, there is a long-felt need in the art for a device that provides economic benefits which include, saving time by speeding up and streamlining the sterilization process, reducing the risk of employee injury and pathogen exposure, and decreasing the number of damaged instruments. Further, there is a long-felt need in the art for a drying rack device that sits on a separate tray which allows for easy disinfection of both the rack and the tray and allows for safe disposal of runoff water that collects in the tray. Finally, there is a long-felt need in the art for a drying rack device that allows several instrument sets to air dry at the same time prior to being packaged for sterilization.

The subject matter disclosed and claimed herein, in one embodiment thereof, comprises a drying rack device. The device is designed to save time and effort when cleaning and sterilizing instruments, tools, and/or accessories. The device comprises a countertop drying rack that sits on a tray. The countertop drying rack comprises a plurality of compartments that can be round and/or flat, with a plurality of drain holes for air drying wet instruments. Further, the tray below the rack collects water runoff for safe disposal and to allow the instruments to air dry. The device keeps instruments and tools organized, different kits separated, allows instruments to dry, and decreases risk of injury and exposure to bloodborne pathogens.

In this manner, the drying rack device of the present invention accomplishes all of the foregoing objectives and provides users with a device that collects water runoff for safe disposal and allows instruments to air dry. The device allows water from wet instruments to drain away and remain in the tray below. The device saves time and efficiency when cleaning and sterilizing instruments.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a drying rack device. The device is designed to save time and effort when cleaning and sterilizing instruments, tools, and/or accessories. The device comprises a countertop drying rack that sits on a tray. The countertop drying rack comprises a plurality of compartments that can be round and/or flat, with a plurality of drain holes for air drying wet instruments. Further, the tray below the rack collects water runoff for safe disposal and to allow the instruments to air dry. The device keeps instruments and tools organized, different kits separated, allows instruments to dry, and decreases risk of injury and exposure to bloodborne pathogens.

In one embodiment, the countertop drying rack of the device comprises a plurality of compartments. Any suitable number of compartments can be utilized as is known in the art, depending on the needs and/or wants of a user. Further, the compartments can be any suitable shape and size as is known in the art as long as the compartments are able to retain a plurality of instruments, tools, and/or accessories. Additionally, different size compartments can be used together, depending on the needs and/or wants of a user. In this embodiment, there are four compartments. The four compartments can be secured together as one integral component or the four compartments can be placed unattached on a tray, or each compartment can be individually secured to a framework on the tray.

In another embodiment, the compartments comprise a round or rectangular base component and two sets of opposing walls. The first set of opposing walls spans the length of the base component, and the second set of opposing walls spans the width of the base component. The walls along with the base component can be round or flat, creating a round trough-like compartment or a rectangular compartment, respectively.

In another embodiment, the compartments comprise a plurality of drain holes in the base component for water to pass through. In this embodiment, the two sets of opposing walls also comprise a plurality of drain holes for airflow. Any number of drain holes can be utilized as is known in the art, depending on the needs and/or wants of a user. Further, the drain holes can be any suitable shape and size as is known in the art, as long as water and/or air can pass therethrough.

In yet another embodiment, the compartments comprise a plurality of feet that keep the compartment spaced from a surface that the device is set upon. The feet provide ventilation under the compartments and help maintain proper temperature control within the device. Typically, there are four feet, one positioned at each corner of the base component. But any suitable number of feet can be utilized as is known in the art.

In another embodiment, the compartments comprise at least one silicone rail underneath the compartments and/or tray to prevent slipping on a counter. Any suitable number of silicone rails can be utilized depending on the needs and/or wants of a user.

In another embodiment, the device comprises a tray positioned below the countertop drying rack that collects water runoff for safe disposal. The tray is disposed below the compartments to catch water and prevent possible corrosion to the bottom of the compartments. The tray may be removed, cleaned, and manually dried when needed. In this embodiment, the tray comprises a base and a wall or lip around the perimeter of the base, such that water is retained within the tray until emptied. The tray is removable and may either slide into the front of the countertop drying rack or, alternatively, the entire countertop drying rack sits on the water collection tray.

In another embodiment, the countertop drying rack is designed for larger instrument cassettes and is needed to isolate and organize such cassettes. Specifically, the countertop drying rack comprises a plurality of divider components secured to a base component and to a wall. The plurality of divider components comprise a plurality of drain holes for airflow to encourage air drying of the cassettes positioned therebetween. The base component also comprises a plurality of drain holes to encourage water to drain away from the cassettes/instruments. A water collection tray is also positioned below the base component to catch contaminated water runoff for safe disposal.

In another embodiment, the countertop drying rack is designed for smaller instrument cassettes (i.e., steri-container cassettes) and is needed to isolate and organize such cassettes. The countertop drying rack may have several individual compartments for smaller cassettes to be stacked in while they air dry. Specifically, the countertop drying rack comprises a plurality of dividers secured to a base component and enclosed by three walls. Typically, the countertop drying rack comprises several levels of compartments, with the base components slanted such that water runs towards the back of each compartment and drips down into a water collection drain tray. Specifically, the base components provide a gap between the base component and the back wall, such that water can run down into a drip tray positioned under the bottom level of compartments. In another embodiment, each row of compartments comprises a water collection tray and the dividers and the base component comprise a plurality of drain holes for airflow and to encourage water to drain away from the cassettes/instruments and into the water collection tray for safe disposal.

In another embodiment, the device can be utilized prior to the instruments and/or cassettes being sterilized, however, in this embodiment, the device can be used post instrument sterilization to encourage cassette and/or packaged instrument cooling and organization when the cassettes are removed from the sterilization equipment, with or without the drain tray.

In one embodiment, the device comprises at least one fan, typically two fans, to generate forced air flow to help dry the instruments inside the device. Further, the device comprises a heating element for heating the air. The fans may remain operational for an additional period of time after the heating element is turned off, typically from about one to about five minutes, usually about three minutes, to cool the device and instruments prior to removal. In some embodiments, the fans may be disposed at air intakes to push air across the heating element and through the device. In other embodiments, the fans may be disposed to push air out of the device, after the air has already passed over the heating element. Further, a control board is provided that receives power and distributes power to the heating element, fans, etc., via batteries or any other suitable power means as is known in the art. An activation button may simultaneously turn on the fans and heating element for a complete drying cycle, typically about 20 minutes. The activation light may illuminate during the cycle. At the end of a heating cycle, typically about 17 minutes, the heating element may turn-off and the fans may remain in operation for an additional period of time. A thermal protector may automatically turn off the unit if the temperature reaches a pre-set maximum, typically about 98° C. This safety preventative measure may be activated if the fans or activation button were to prematurely fail, become clogged, etc.

In yet another embodiment, the drying rack device is manufactured from heat-sealable plastic or polymers, such as polypropylene or acrylonitrile-butadiene-styrene (ABS), metals, such as stainless steel, etc.

In yet another embodiment, the drying rack device is manufactured from a material that is water resistant.

In another embodiment, the drying rack device comprises a plurality of indicia.

In yet another embodiment, a method of organizing and drying sets of instruments before the sterilization process is described. The method includes the steps of providing a drying rack device comprising a countertop drying rack with a plurality of compartments which sit on a tray. The method also comprises positioning the plurality of instruments from the ultrasonic cleaner into the plurality of compartments. Further, the method comprises allowing the plurality of instruments to air dry within the device. The method comprises collecting water runoff for safe disposal in the tray below the countertop drying rack. Finally, transferring the instruments out of the device for sterilization or sterilizing the instruments and the device together.

In differing embodiments, the size of the countertop drying rack, the number of cassettes/instruments each row holds, and the size/type of cassette each row holds may vary, depending on the needs and/or wants of a user.

Numerous benefits and advantages of this invention will become apparent to those skilled in the art to which it pertains, upon reading and understanding the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
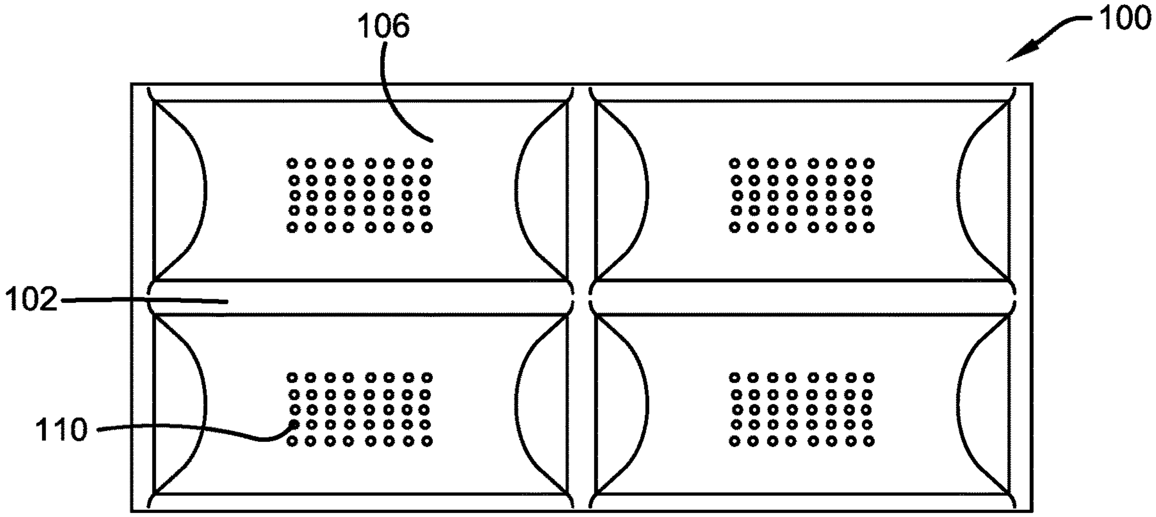
FIG. 1 illustrates a top perspective view of one embodiment of the drying rack device of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long-felt need in the art for a drying rack device that provides users with a compartmentalized rack that keeps several instrument sets and cassettes organized while they dry, eliminating the need to sort them and increasing efficiency. There is also a long-felt need in the art for a drying rack device that eliminates the problem of instrument sets repeatedly being dumped on top of one another and rewetting the entire pile. Further, there is a long-felt need in the art for a drying rack device that features compartments with drain holes and that sits on an accompanying tray. Moreover, there is a long-felt need in the art for a device that provides economic benefits which include, saving time by speeding up and streamlining the sterilization process, reducing the risk of employee injury and pathogen exposure, and decreasing the number of damaged instruments. Further, there is a long-felt need in the art for a drying rack device that sits on a separate tray which allows for easy disinfection of both the rack and the tray and allows for safe disposal of runoff water that collects in the tray. Finally, there is a long-felt need in the art for a drying rack device that allows several instrument sets to air dry at the same time prior to being packaged for sterilization.

The present invention, in one exemplary embodiment, is a novel drying rack device. The device is designed to save time and effort when cleaning and sterilizing instruments, tools, and/or accessories. The device comprises a countertop drying rack that sits on a tray. The countertop drying rack comprises a plurality of compartments that can be round and/or flat, with a plurality of drain holes for air drying wet instruments. Further, the tray below the rack collects water runoff for safe disposal and to allow the instruments to air dry. The present invention also includes a novel method of organizing and drying sets of instruments before the sterilization process. The method includes the steps of providing a drying rack device comprising a countertop drying rack with a plurality of compartments which sit on a tray. The method also comprises positioning the plurality of instruments from the ultrasonic cleaner into the plurality of compartments. Further, the method comprises allowing the plurality of instruments to air dry within the device. The method comprises collecting water runoff for safe disposal in the tray below the countertop drying rack. Finally, transferring the instruments out of the device for sterilization or sterilizing the instruments and the device together.

Referring initially to the drawings, FIG. 1 illustrates a perspective view of one embodiment of the drying rack device 100 of the present invention. In the present embodiment, the drying rack device 100 is an improved drying rack device that quickly and efficiently air dries instruments, tools, and accessories. The device 100 is especially designed to allow anyone that utilizes dental, medical, orthodontic, and/or veterinary tools, instruments, and/or accessories, etc., or any other suitable user as is known in the art, to easily and efficiently air dry instruments before sterilization. More specifically, the device 100 comprises a countertop drying rack 102 that sits on a water collection tray 104. The countertop drying rack 102 comprises a plurality of compartments 106 for retaining a plurality of instruments 108, and wherein the plurality of compartments 106 comprise a plurality of drain holes 110 for air drying or for water to drip down into the collection tray 104. Further, the collection tray 104 below the rack 102, collects water runoff for safe disposal and to allow the instruments 108 to air dry. Thus, the device 100 keeps instruments 108 and tools organized, different kits separated, allows instruments 108 to dry, and decreases risk of injury and exposure to bloodborne pathogens.

Figure 2:
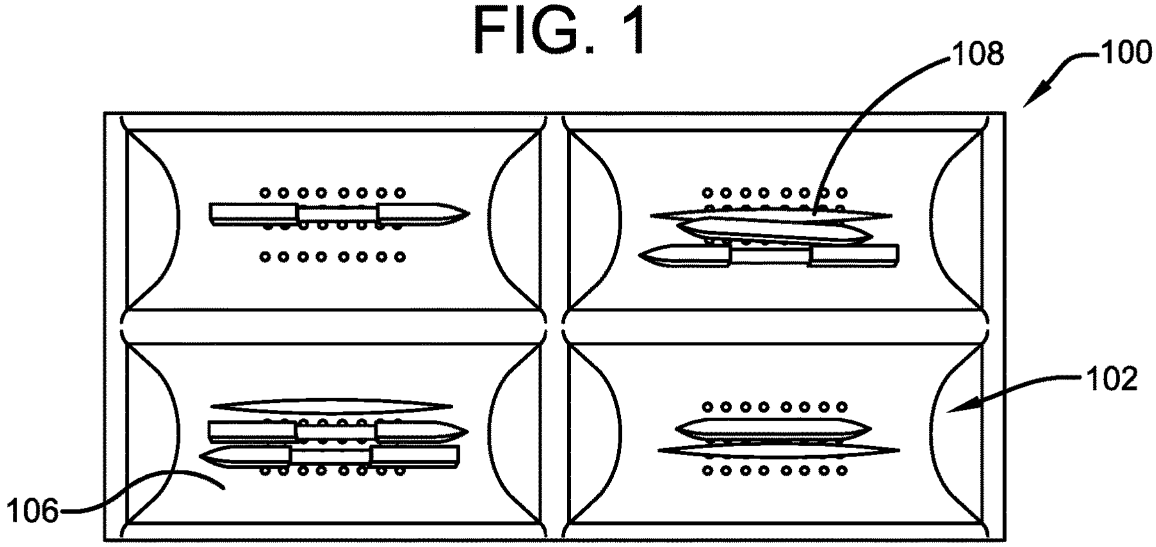
FIG. 2 illustrates a top perspective view of one embodiment of the drying rack device of the present invention wherein the compartments comprise a plurality of instruments in accordance with the disclosed architecture.

As shown in FIG. 2, the countertop drying rack 102 of the device 100 comprises a plurality of compartments 106. Any suitable number of compartments 106 can be utilized as is known in the art, depending on the needs and/or wants of a user. Further, the compartments 106 can be any suitable shape and size as is known in the art as long as the compartments 106 are able to retain a plurality of instruments 108, tools, and/or accessories. Additionally, different size compartments 106 can be used together, depending on the needs and/or wants of a user. In this embodiment, there are four compartments 106. The four compartments 106 can be secured together as one integral component or the four compartments 106 can be placed unattached on the collection tray 104, or each compartment 106 can be individually secured to a framework on the collection tray 104.

Furthermore, the compartments 106 comprise a rounded or rectangular base component 112 and two sets of opposing walls 114, 116. The first set of opposing walls 114 spans the length of the base component 112 and the second set of opposing walls 116 spans the width of the base component 112. The walls 114, 116 along with the base component 112 can be round or flat, creating a rounded trough-like compartment or a rectangular compartment, respectively.

Figure 3:
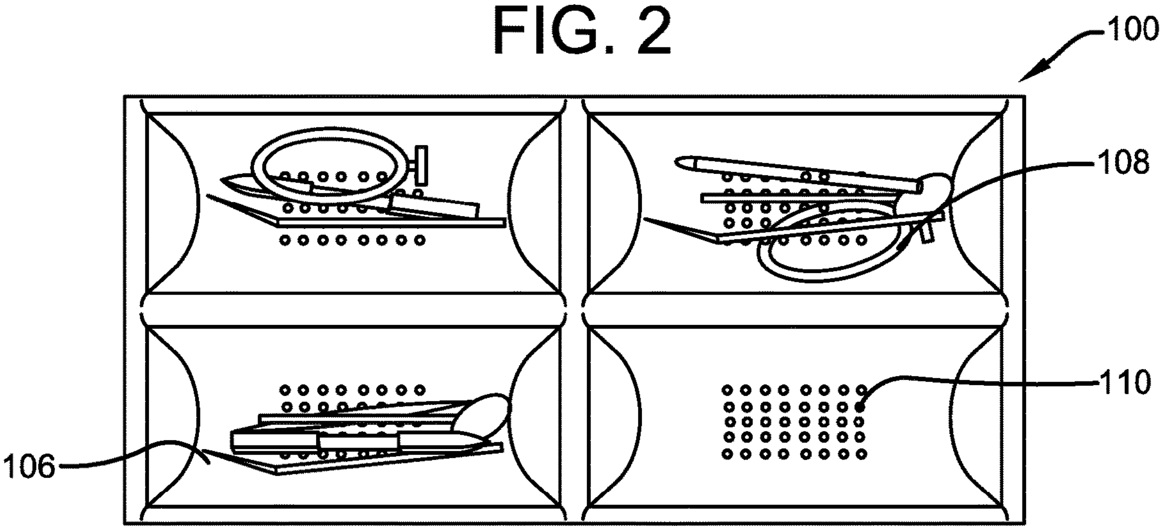
FIG. 3 illustrates a top perspective view of one embodiment of the drying rack device of the present invention wherein the compartments comprise a plurality of tools and accessories in accordance with the disclosed architecture.

As shown in FIG. 3, the compartments 106 comprise a plurality of drain holes 110 in the base component 112 for water to pass through. In this embodiment, the two sets of opposing walls 114, 116 also comprise a plurality of drain holes 110 for airflow. Any number of drain holes 110 can be utilized as is known in the art, depending on the needs and/or wants of a user. Further, the drain holes 110 can be any suitable shape and size as is known in the art, such as circular, oval, oblong, rectangular, square, etc., as long as water and/or air can pass therethrough.

Figure 4:
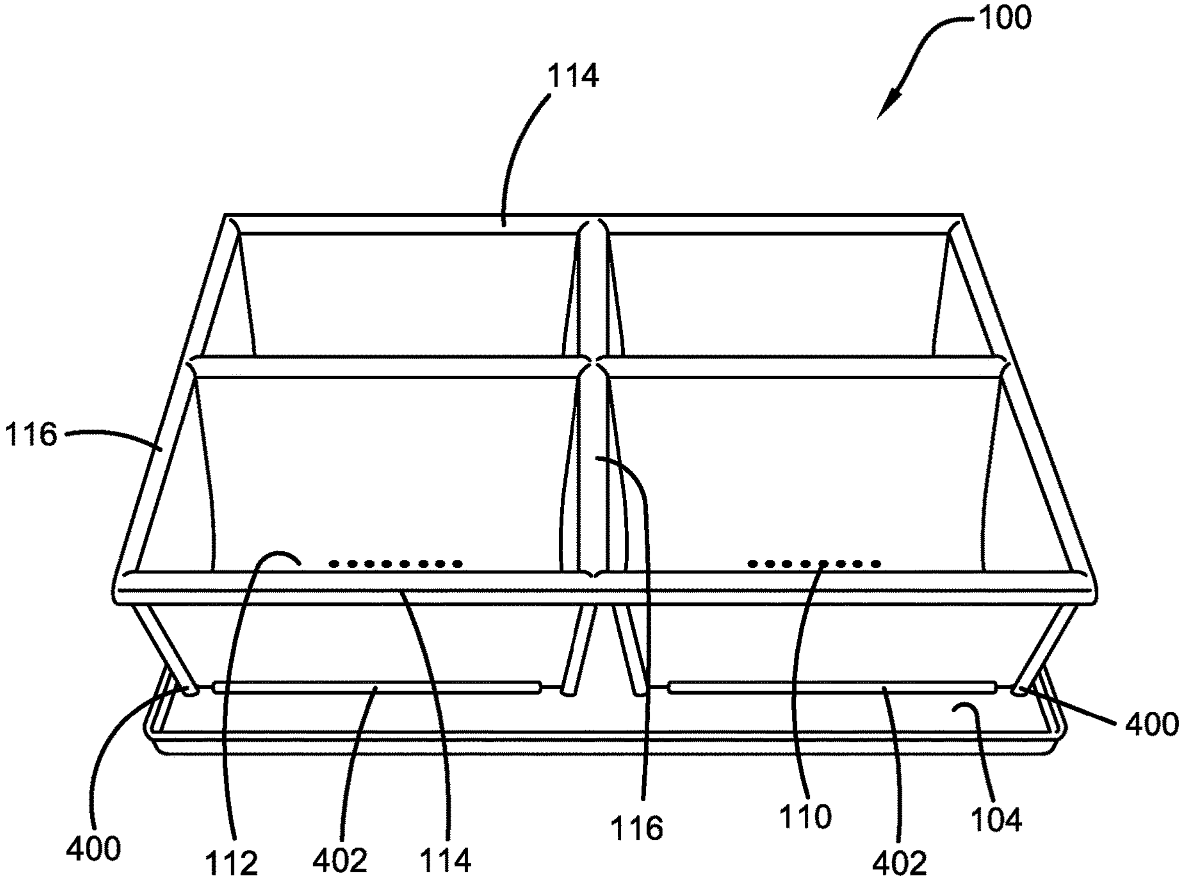
FIG. 4 illustrates a side perspective view of one embodiment of the drying rack device of the present invention showing the tray in accordance with the disclosed architecture.

As shown in FIG. 4, the compartments 106 comprise a plurality of feet 400 that keep the compartment 106 spaced from the surface that the device 100 is set upon, typically the water collection tray 104. The feet 400 provide ventilation under the compartments 106 and help maintain proper temperature control within the device 100. Typically, there are four feet 400, one positioned at each corner of the base component 112. But any suitable number of feet 400 can be utilized as is known in the art.

Furthermore, the device 100 comprises a tray 104 positioned below the countertop drying rack 102 that collects water runoff for safe disposal. The tray 104 is disposed below the compartments 106 to catch water and prevent possible corrosion to the bottom of the compartments 106. The tray 104 may be removed, cleaned, and manually dried when needed. In this embodiment, the tray 104 comprises a base 404 and a wall or lip 406 around the perimeter of the base 404, such that water is retained within the tray 104 until emptied. The tray 104 is removable and may either slide into the front of the countertop drying rack 102 or, alternatively, the entire countertop drying rack 102 sits on the water collection tray 104.

In another embodiment, the compartments 106 comprise at least one silicone rail 402 underneath the compartments 106 and/or tray 104 to prevent slipping on a counter. Any suitable number of silicone rails 402 can be utilized depending on the needs and/or wants of a user. Further, the silicone rails 402 can be any suitable shape and size as is known in the art. The silicone rails 402 secured to the bottom of the compartments 106 prevent slipping of the compartments 106 within the tray 104. The silicone rails 402 secured to the bottom of the tray 104 prevent slipping of the tray 104 on the counter or other suitable work surface.

Figure 5:
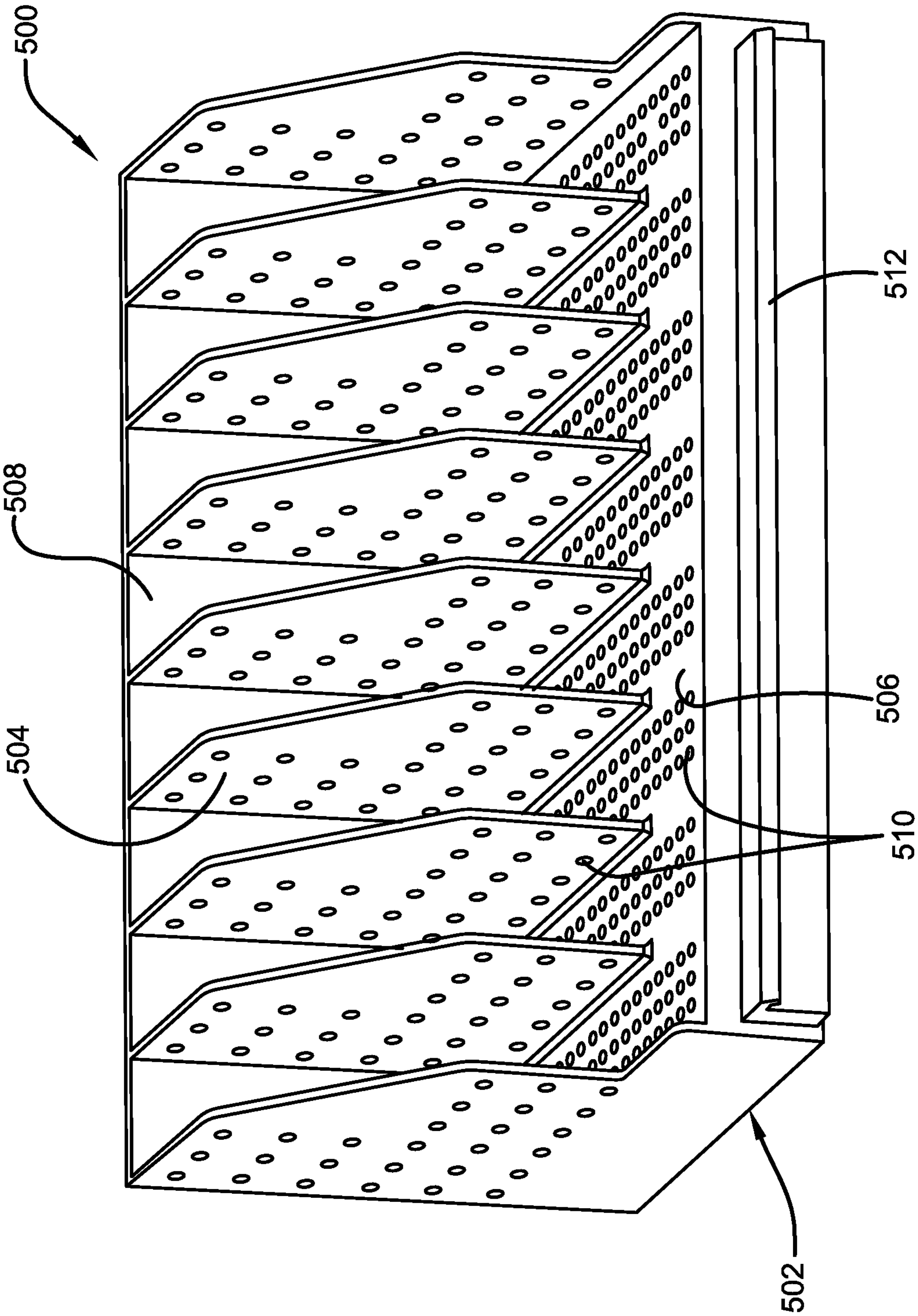
FIG. 5 illustrates a front perspective view of one embodiment of the drying rack device of the present invention wherein the compartments hold larger instrument cassettes in accordance with the disclosed architecture.

As shown in FIG. 5, this embodiment of the drying rack device 500 comprises a countertop drying rack 502 that is designed for larger instrument cassettes and is needed to isolate and organize such cassettes. Specifically, the countertop drying rack 502 comprises a plurality of divider components 504 secured to a base component 506 and to a wall 508. Any suitable number of divider components 504 can be utilized as is known in the art, depending on the needs and/or wants of a user. Further, the plurality of divider components 504 comprise a plurality of drain holes 510 for airflow, to encourage air drying of the cassettes positioned therebetween. The base component 506 also comprises a plurality of drain holes 510 to encourage water to drain away from the cassettes/instruments. A water collection tray 512 is also positioned below the base component 506 to catch contaminated water runoff for safe disposal. As stated supra, the water collection tray 512 is removable and may either slide into the front of the countertop drying rack 502 or, alternatively, the entire countertop drying rack 502 can sit on the water collection tray 512.

Figure 6:
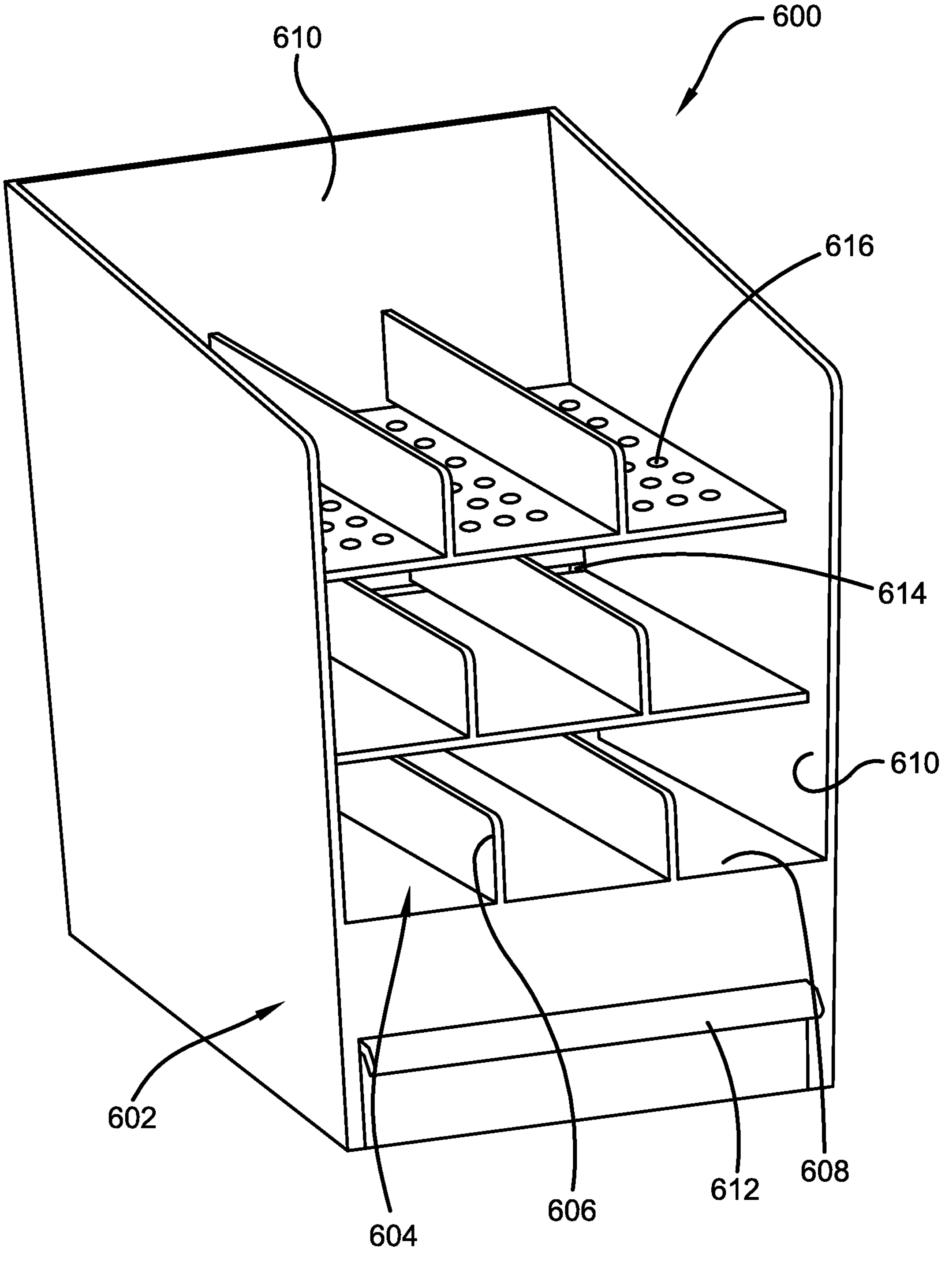
FIG. 6 illustrates a front perspective view of one embodiment of the drying rack device of the present invention wherein the compartments hold smaller instrument cassettes in accordance with the disclosed architecture.

As shown in FIG. 6, this embodiment of the drying rack device 600 comprises a countertop drying rack 602 that is designed for smaller instrument cassettes (i.e., steri-container cassettes) and is needed to isolate and organize such cassettes. The countertop drying rack 602 may have several individual compartments 604 for smaller cassettes to be stacked in while they air dry. Specifically, the countertop drying rack 602 comprises a plurality of dividers 606 secured to a base component 608 and enclosed by three walls 610. Typically, the countertop drying rack 602 comprises several levels of compartments 604, with the base components 608 slanted such that water runs towards the back of each compartment 604 and drips down into a water collection drain tray 612. Any suitable number of dividers and/or number of rows or levels of compartments 604 can be utilized as is known in the art, depending on the needs and/or wants of a user. Specifically, the base components 608 would provide a space or gap 614 between the base component 608 and the back wall 610, such that water can run down into the water collection tray 612 positioned under the bottom level of compartments 604. In another embodiment, each row of compartments 604 comprises a water collection tray 612, and the dividers 606 and the base component 608 comprise a plurality of drain holes 616 for airflow and to encourage water to drain away from the cassettes/instruments and into the water collection tray 612 for safe disposal.

Figure 7:
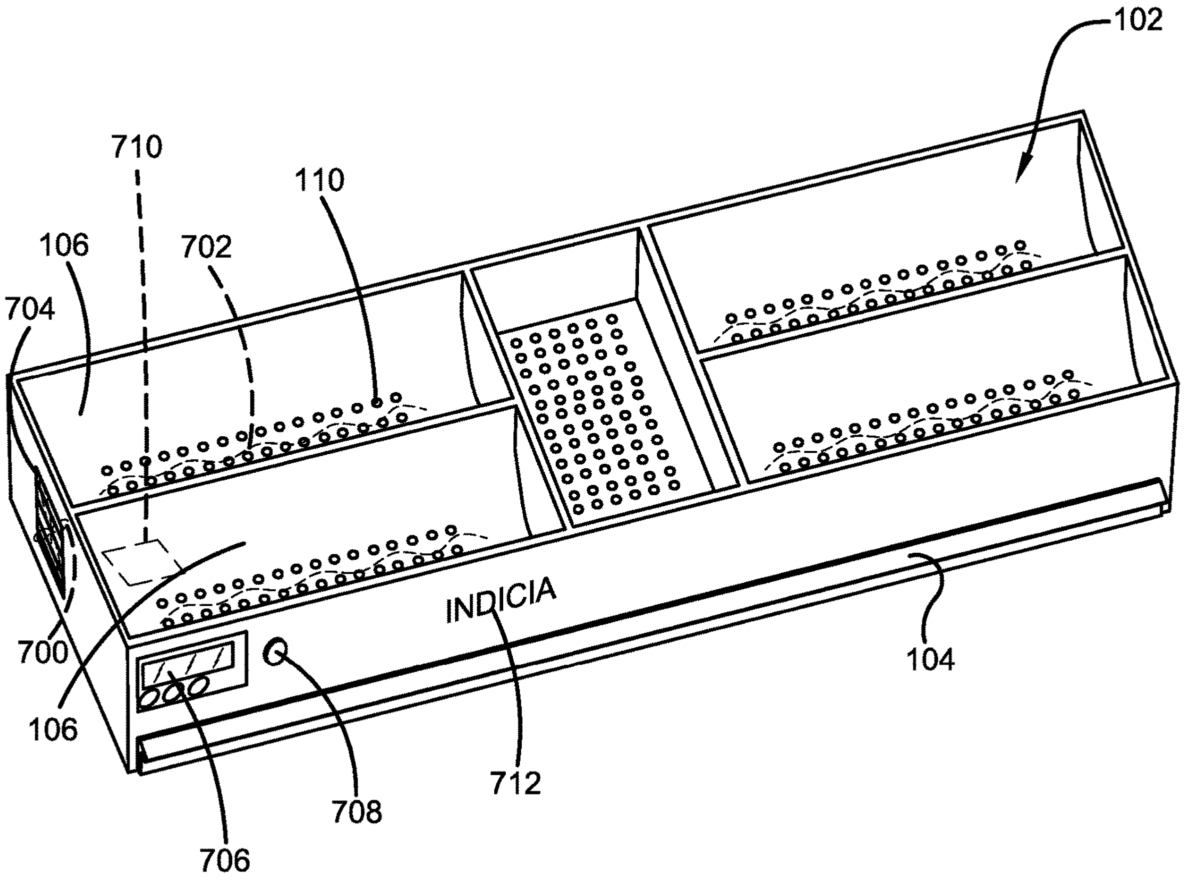
FIG. 7 illustrates a top perspective view of one embodiment of the drying rack device of the present invention in accordance wherein the compartments comprise a plurality of drain holes with the disclosed architecture.

As shown in FIG. 7, the compartments 106 can be any suitable shape and size as is known in the art, as long as the compartments 106 are able to retain a plurality of instruments 108, tools, and/or accessories. Additionally, different sized compartments 106 can be used together, depending on the needs and/or wants of a user.

Furthermore, the device 100 can be utilized prior to the instruments 108 and/or cassettes being sterilized, however, in this embodiment, the device 100 can be used post instrument sterilization to encourage cassette and/or packaged instrument cooling and organization when the cassettes are removed from the sterilization equipment, with or without the drain tray 104.

Additionally, in one embodiment, the device 100 comprises at least one fan 700, typically two fans 700, to generate forced air flow to help dry the instruments 108 inside the device 100. Further, the device 100 comprises a heating element 702 for heating the air. The fans 700 may remain operational for an additional period of time after the heating element 702 is turned off, typically from about one to about five minutes, usually about three minutes, to cool the device 100 and instruments 108 prior to removal. In some embodiments, the fans 700 may be positioned at air intakes 704 to push air across the heating element 702 and through the device 100. In other embodiments, the fans 700 may be disposed to push air out of the device 100, after the air has already passed over the heating element 702.

Further, a control board 706 is provided that receives power and distributes power to the heating element 702, fans 700, etc., via batteries or any other suitable power means as is known in the art. An activation button 708 may simultaneously turn on the fans 700 and the heating element 702 for a complete drying cycle, typically about 20 minutes. The activation light 708 may illuminate during the cycle. At the end of a heating cycle, typically about 17 minutes, the heating element 702 may turn-off and the fans 700 may remain in operation for an additional period of time. A thermal protector 710 may automatically turn off the unit if the temperature reaches a pre-set maximum, typically about 98° C. This safety preventative measure may be activated if the fans 700 or activation button 708 were to prematurely fail, become clogged, etc.

In differing embodiments, the size of the countertop drying rack 102, the number of cassettes/instruments 108 each row holds, and the size/type of cassette each row holds may vary, depending on the needs and/or wants of a user.

In yet another embodiment, the drying rack device 100 is manufactured from heat-sealable plastic or polymers, such as polypropylene or acrylonitrile-butadiene-styrene (ABS), or any other suitable material as is known in the art, such as, but not limited to, acrylic, polycarbonate, polyethylene, thermoplastic, polyethylene, polyethylene terephthalate, polyvinyl chloride, polystyrene, metals, such as stainless steel, etc. Generally, the drying rack device 100 is also manufactured from a material that is water resistant or water permeable, or the countertop drying rack 102 comprises a coating that is water resistant or water permeable.

In another embodiment, the drying rack device 100 comprises a plurality of indicia 712. Specifically, the countertop drying rack 102 of the device 100 may include advertising, a trademark, or other letters, designs, or characters, printed, painted, stamped, or integrated into the countertop drying rack 102, or any other indicia 712 as is known in the art. Specifically, any suitable indicia 712 as is known in the art can be included, such as, but not limited to, patterns, logos, emblems, images, symbols, designs, letters, words, characters, animals, advertisements, brands, etc., that may or may not be drawing or instrument/brand related.

Figure 8:
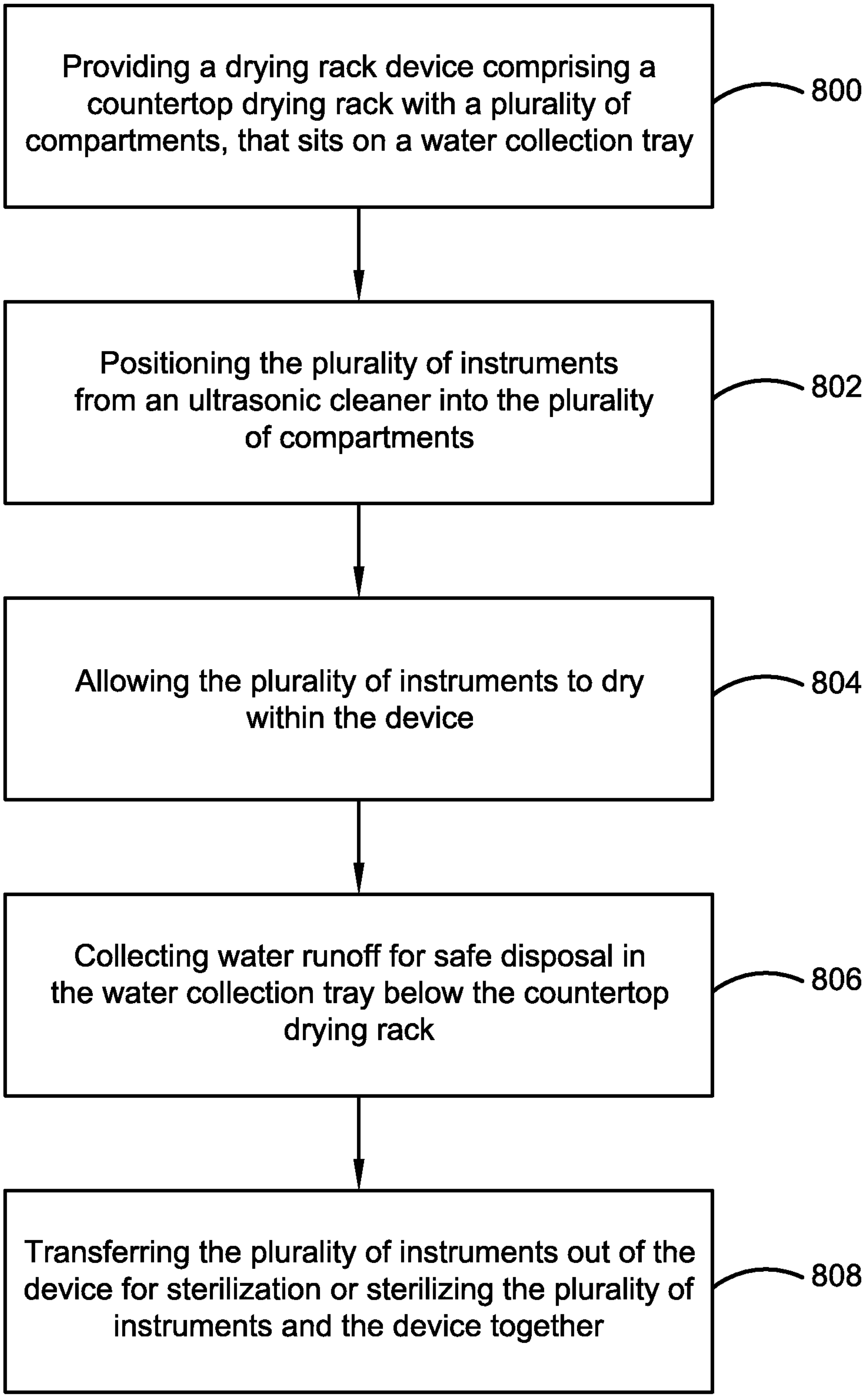
FIG. 8 illustrates a flowchart showing the method of organizing and drying sets of instruments before the sterilization process in accordance with the disclosed architecture.

FIG. 8 illustrates a flowchart of the method of organizing and drying sets of instruments before the sterilization process. The method includes the steps of at 800, providing a drying rack device comprising a countertop drying rack with a plurality of compartments which sit on a tray. The method also comprises at 802, positioning the plurality of instruments from the ultrasonic cleaner into the plurality of compartments. Further, the method comprises at 804, allowing the plurality of instruments to air dry within the device. The method comprises at 806, collecting water runoff for safe disposal in the tray below the countertop drying rack. Finally, at 808, transferring the instruments out of the device for sterilization or sterilizing the instruments and the device together.

Figure 9:
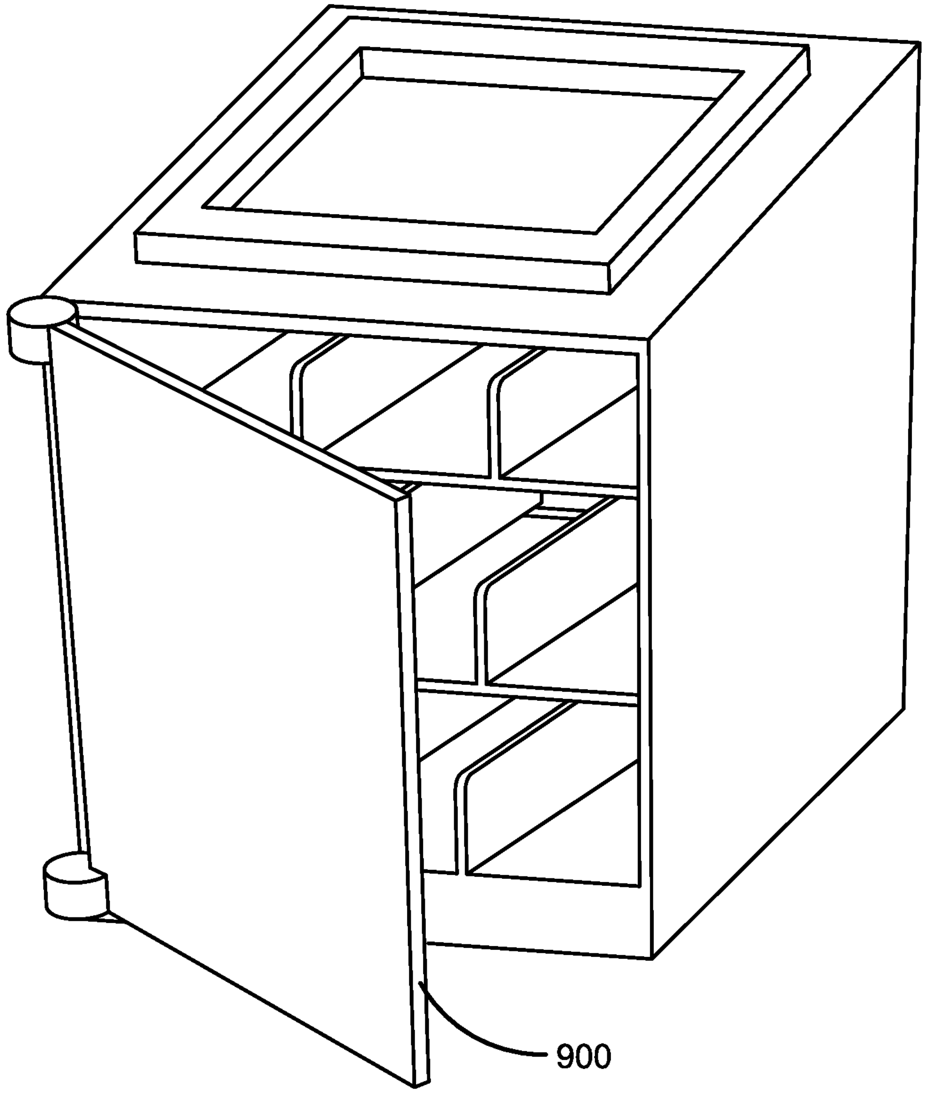
FIG. 9 illustrates a front perspective view of one potential embodiment of the drying rack device of the present invention with a door in accordance with the disclosed architecture.

FIG. 9 illustrates a front perspective view of one potential embodiment of the drying rack device 100 of the present invention with a door in accordance with the disclosed architecture. The various drying racks may be stacked on top of one another, and the door 900 hingedly attached to the cabinet to be repositioned. Further, the entire cabinet may be enclosed.

Certain terms are used throughout the following description and claims to refer to particular features or components. As one skilled in the art will appreciate, different users may refer to the same feature or component by different names. This document does not intend to distinguish between components or features that differ in name but not structure or function. As used herein "drying rack device" and "device" are interchangeable and refer to the drying rack device 100 of the present invention.

Notwithstanding the foregoing, the drying rack device 100 of the present invention can be of any suitable size and configuration as is known in the art without affecting the overall concept of the invention, provided that it accomplishes the above-stated objectives. One of ordinary skill in the art will appreciate that the drying rack device 100 as shown in FIGS. 1-8 are for illustrative purposes only, and that many other sizes and shapes of the drying rack device 100 are well within the scope of the present disclosure. Although the dimensions of the drying rack device 100 are important design parameters for user convenience, the drying rack device 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A drying rack device for quickly and efficiently air drying a plurality of instruments, tools and accessories, the drying rack device comprising:

a countertop drying rack comprising a plurality of compartments; and a water collection tray positioned below the countertop drying rack;

a heating element; and a pair of fans configured to blow air across the heating element; and wherein the plurality of compartments are sized and configured to retain the plurality of instruments, tools and accessories;

wherein the plurality of compartments comprise a plurality of drain holes for a liquid to pass through;

wherein the water collection tray collects the liquid passing through the plurality of drain holes;

wherein the plurality of instruments, tools and accessories can be air-dried via a flow of air passing through the plurality of drain holes; and wherein each of the plurality of compartments and the water collection tray comprises a plurality of silicon rails configured to prevent slippage.

2. The drying rack device of claim 1, wherein the plurality of compartments comprise a rounded base component.

3. The drying rack device of claim 2, wherein the plurality of compartments further comprise two sets of opposing walls.

4. The drying rack device of claim 3, wherein the rounded base component comprises a plurality of drain holes.

5. The drying rack device of claim 4, wherein the two sets of opposing walls comprise a plurality of drain holes.

6. The drying rack device of claim 5, wherein the plurality of compartments comprise a plurality of feet.

7. The drying rack device of claim 1, wherein the water collection tray is repositionable relative to the countertop drying rack.

8. The drying rack device of claim 7, wherein the water collection tray is slid into a front of the countertop drying rack.

9. The drying rack device of claim 7, wherein the countertop drying rack sits on the water collection tray.

10. A drying rack device for air drying a plurality of instrument cassettes, the drying rack device comprising:

a base component;

a wall;

a plurality of divider components secured to the base component and to the wall;

a water collection tray positioned below the plurality of divider components, wherein the plurality of divider components retain the plurality of instrument cassettes, and further wherein the plurality of instrument cassettes are air-dried via a flow of air;

a heating element;

a pair of fans configured to blow air across the heating element;

a control board that distributes power to the heating element and the pair of fans; and a thermal protector configured to turn off the heating element if a pre-set temperature is exceeded.

11. The drying rack device of claim 10, wherein the water collection tray is repositionable relative to the base component and the plurality of divider components comprise a plurality of drain holes for a liquid to pass through, and further wherein the water collection tray collects the liquid passing through the plurality of drain holes.

12. The drying rack device of claim 11, wherein a plurality of rows of divider components can be utilized.

13. The drying rack device of claim 12, wherein the plurality of divider components are arranged in a slant.

14. The drying rack device of claim 13, wherein a gap is formed between the base component and a back wall, such that the liquid runs towards the gap.

15. The drying rack device of claim 14, wherein the water collection tray is positioned underneath each of the plurality of rows of divider components.

16. The drying rack device of claim 15 further comprising a plurality of indicia.

17. A method of organizing and drying a plurality of instruments before a sterilization process, the method comprising:

providing a drying rack device comprising a countertop drying rack with a plurality of compartments and a water collection tray;

positioning the plurality of instruments from an ultrasonic cleaner into the plurality of compartments;

allowing the plurality of instruments to air dry within the plurality of compartments;

collecting a liquid runoff for safe disposal in the water collection tray below the countertop drying rack; and transferring the plurality of instruments out of the drying rack device for sterilization or sterilizing the plurality of instruments and the drying rack device together.

* * * * *